United States Patent [19]

Quedens et al.

[11] Patent Number: 5,168,876
[45] Date of Patent: Dec. 8, 1992

[54] CONNECTOR DEVICE FOR USE IN MONITORING FETAL HEART RATE

[75] Inventors: Phillipp J. Quedens, Berlin; Donald R. Boucher, Wallingford; John T. Shipherd, Madison; James W. Poirier, Northford; Joseph A. Izzo, New Haven, all of Conn.

[73] Assignee: American Home Products Corporation, New York, N.Y.

[21] Appl. No.: 661,253

[22] Filed: Feb. 26, 1991

Related U.S. Application Data

[63] Continuation-in-part of Ser. No. 605,843, Oct. 30, 1990.

[51] Int. Cl.⁵ .............................................. A61B 5/04
[52] U.S. Cl. ................................................... 128/642
[58] Field of Search ............................. 128/639–642, 128/698, 783–785; 439/530, 668, 669, 877, 909, 825, 842, 851, 852, 856

[56] References Cited

U.S. PATENT DOCUMENTS

| | | |
|---|---|---|
| Re. 28,990 | 10/1976 | Hon et al. ............................ 128/639 |
| Re. 32,204 | 7/1986 | Halvorsen ........................... 128/642 |
| 2,318,207 | 5/1943 | Ellis .................................... 128/644 |
| 3,580,242 | 5/1971 | La Croix ............................. 128/642 |
| 3,800,800 | 4/1974 | Garbe et al. ........................ 128/408 |
| 3,895,635 | 7/1975 | Justus et al. ........................ 128/639 |
| 4,061,408 | 12/1977 | Bast et al. .......................... 339/75 R |
| 4,073,287 | 2/1978 | Bradley et al. ..................... 128/642 |
| 4,090,760 | 5/1978 | Eurey .................................. 128/639 |
| 4,094,571 | 6/1978 | Benjamin ............................ 339/91 R |
| 4,121,573 | 10/1978 | Crovella et al. . |
| 4,180,080 | 12/1979 | Murphy .............................. 128/642 |
| 4,209,020 | 6/1980 | Nielsen ............................... 128/640 |
| 4,253,721 | 3/1981 | Kaufman ............................ 339/91 R |
| 4,268,101 | 5/1981 | Stone .................................. 339/61 R |
| 4,320,764 | 3/1982 | Hon .................................... 128/642 |
| 4,321,931 | 3/1982 | Hon .................................... 128/642 |
| 4,353,372 | 10/1982 | Ayer ................................... 128/640 |
| 4,384,757 | 5/1983 | Andrews, Jr. et al. ........... 339/258 R |
| 4,437,467 | 3/1984 | Helfer et al. ....................... 128/642 |
| 4,522,211 | 6/1985 | Bare et al. .......................... 128/604 |
| 4,632,121 | 12/1986 | Johnson et al. .................... 128/639 |
| 4,671,591 | 6/1987 | Archer ................................ 439/346 |
| 4,848,345 | 7/1989 | Zenkich .............................. 128/419 D |
| 4,894,023 | 1/1990 | Hall .................................... 439/278 |
| 4,911,657 | 3/1990 | Berlin ................................. 439/502 |
| 5,046,965 | 9/1991 | Neese et al. ........................ 128/642 |

FOREIGN PATENT DOCUMENTS

| | | |
|---|---|---|
| 0377432 | 7/1990 | European Pat. Off. . |
| 8603542 | 5/1986 | Fed. Rep. of Germany . |
| 8701828 | 4/1987 | Fed. Rep. of Germany . |
| 1339029 | 11/1973 | United Kingdom . |
| 2057784 | 2/1980 | United Kingdom . |

OTHER PUBLICATIONS

Corometrics Medical Systems, Inc., Leg Plate for Use with Corometrics Model 115, 116 Fetal Monitors, as offered for sale in Catalog No. 2608DAO, Sep. 1988, 5 pp.

Primary Examiner—Lee S. Cohen
Assistant Examiner—Jeffrey R. Jastrzab
Attorney, Agent, or Firm—Darby & Darby

[57] ABSTRACT

A connector device interposed between a fetal heart rate monitor and fetal and material electrodes. The device includes a connector inserted in a leg plate. The leg plate has a housing which contains a printed circuit board. The board or housing is detachably connected to a base. The board has tracers which interconnect output terminals of the housing with input contacts of the housing and with a ground electrode of the base. The output terminals lead to the fetal heart rate monitor. The input contacts are in electrical contact with terminals of the connector, which in turn are electrically connected with the electrodes via a twisted wire pair. The input contacts of the leg plate are preferably in the form of barrel contacts which have fingers whose free ends either electrically connect with the connector terminals or engage with a recess on an exterior periphery of the connector.

22 Claims, 8 Drawing Sheets

Fig. 19. PRIOR ART

CONNECTOR DEVICE FOR USE IN MONITORING FETAL HEART RATE

CROSS-REFERENCE TO COPENDING APPLICATIONS

This is a continuation-in-part of U.S. patent application Ser. No. 07/605,843, filed Oct. 30, 1990.

BACKGROUND OF THE INVENTION

1. Field of the Invention

The present invention relates to a connector device for use in monitoring fetal heart rate. The device electrically interconnects a remote fetal monitor with fetal and maternal electrodes by employing a twisted wire pair with plug connector and leg plate.

2. Discussion of Related Art

The contents of U.S. patent application Ser. No. 605,843 of the same assignee is incorporated herein by reference. As discussed therein, a fetal electrode product is provided which avoids the need for handling loose wire ends when connecting the product to input contacts in an opening of a leg plate housing. This fetal electrode product includes a twisted wire pair interconnecting two connector terminals of a plug connector with fetal and maternal electrodes, respectively.

This fetal electrode product is fine for avoiding the handling of loose wires to effect electrical connection by providing for the plug connector, which is to be inserted within the opening in the leg plate housing. The leg plate housing is convenient for establishing electrical connection between the inserted plug connector and output terminals that are in electrical connection with a fetal monitor.

While the establishment of electrical connection between the plug connector terminals and the leg plate input contacts may be verified by looking through a window in the leg plate, customers may find it more desireable to verify this establishment of electrical connection by using the sense of touch. Also, if the plug connector could be locked in position within the housing, it would have less of a potential for inadvertently falling out.

Further, the assembly of the housing requires that wires be extended from the input contacts to the output terminals. The wires of the fetal electrode product and those in the leg plate may be color coded to ensure that the fetal and maternal electrodes become associated with the proper output terminals. Otherwise, mismatching may arise which would lead to misinterpretation of the sensed signals from the electrodes by the fetal monitor.

This assembly may be simplified if the wires in the leg plate did not have to be extended fully between the input contacts and the output terminals. Also, the need for some of this color coding of the wires could be obviated if the order of relative arrangement of the electrodes, connector terminals and input contacts with respect to each other were predetermined to make association of each electrode with an associated input contact evident because of their relative arrangement.

As may be appreciated, signals are transmitted from the electrodes and along respective paths to the fetal monitor. Any break in these paths will adversely affect receipt of the transmitted signals. It would therefore be desireable to be able to detect where in the paths such breaks occur.

SUMMARY OF THE INVENTION

The present invention is directed to a connector device for use in monitoring fetal heart rate. The connector device preferably includes a fetal electrode product and a leg plate.

The fetal electrode product includes fetal and maternal electrodes, a plug connector with two connector terminals and a twisted wire pair. Each wire of the pair extends between and electrically connects a respective electrode with a corresponding one of the two connector terminals. The plug connector preferably has a recess about a portion of its periphery.

The leg plate has a housing with a housing opening. Preferably, the leg plate also has a base which is secured to the housing and which has a ground electrode. In the housing opening may be two input contacts spaced from each other; one input contact is between the entrance of the housing opening and the other input contact. The housing opening with the two input contacts constitutes a socket for retaining the plug connector when inserted therein so that the two connector terminals make electrical contact with the two input contacts, respectively.

The housing preferably contains a printed circuit board which has conductive tracers. The tracers electrically connect the input contacts and the ground electrode with respective output leads. These output leads extend from the printed circuit board and are in electrical connection with a fetal monitor. Thus, respective conductive paths are formed which include the conductive tracers, the output leads and electrical connection with the fetal monitor.

Further, test leads may be provided on the printed circuit board for testing signal transmission through these conductive paths and through the fetal monitor. In this manner, it is possible to detect whether there is a break in the paths and whether the fetal monitor is properly responding to receipt of signals.

BRIEF DESCRIPTION OF THE DRAWINGS

For a better understanding of the present invention, reference is made to the following description and accompanying drawings, while the scope of the invention is set forth in the appended claims.

DESCRIPTION OF THE PREFERRED EMBODIMENT

Figure 1:
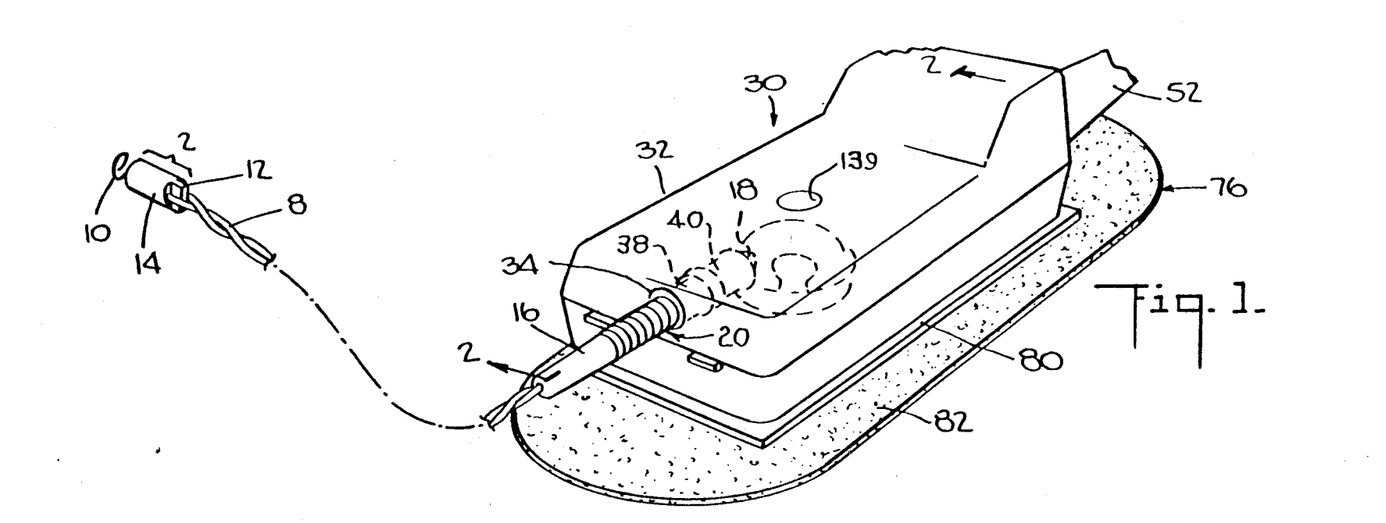
FIG. 1 shows a perspective view of a first embodiment of a connector device for use in monitoring fetal heart rate in accordance with the invention.

FIG. 1 shows a forward wire end 2 of a conventional fetal electrode product in accordance with U.S. Pat. No. Re. 28,990. The fetal electrode product includes a twisted pair of wires 8 whose ends are connected to respective fetal and maternal electrodes 10, 12. A nonconductive plastic holder 14 electrically insulates the fetal and maternal electrodes 10, 12 from each other. The twisted wire pair 8 extends through a finned thermoplastic strain relief element 16 into a connector 20 in accordance with the invention.

Figure 19:
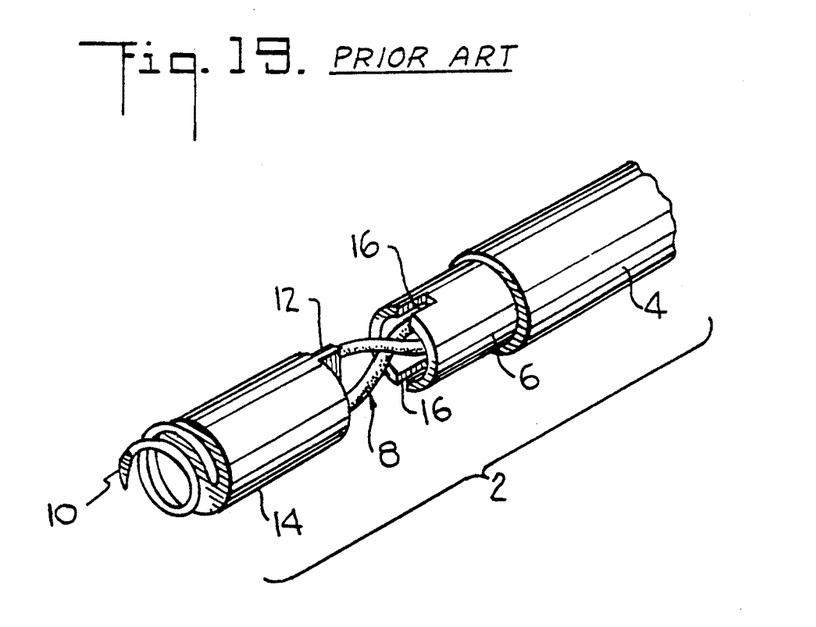
FIG. 19 is a perspective view of the forward end of a bipolar fetal electrode assembly in accordance with the prior art.

For the sake of brevity, a discussion concerning the procedure for engagement of the fetal electrode 10 with a fetus and the removal of guide and, driving tubes (not shown) with a drive handle 4,6 (see FIG. 19) is not repeated here in view of the discussion and illustration of this procedure in U.S. patent application 605,843.

Figures 4, 5, 6:
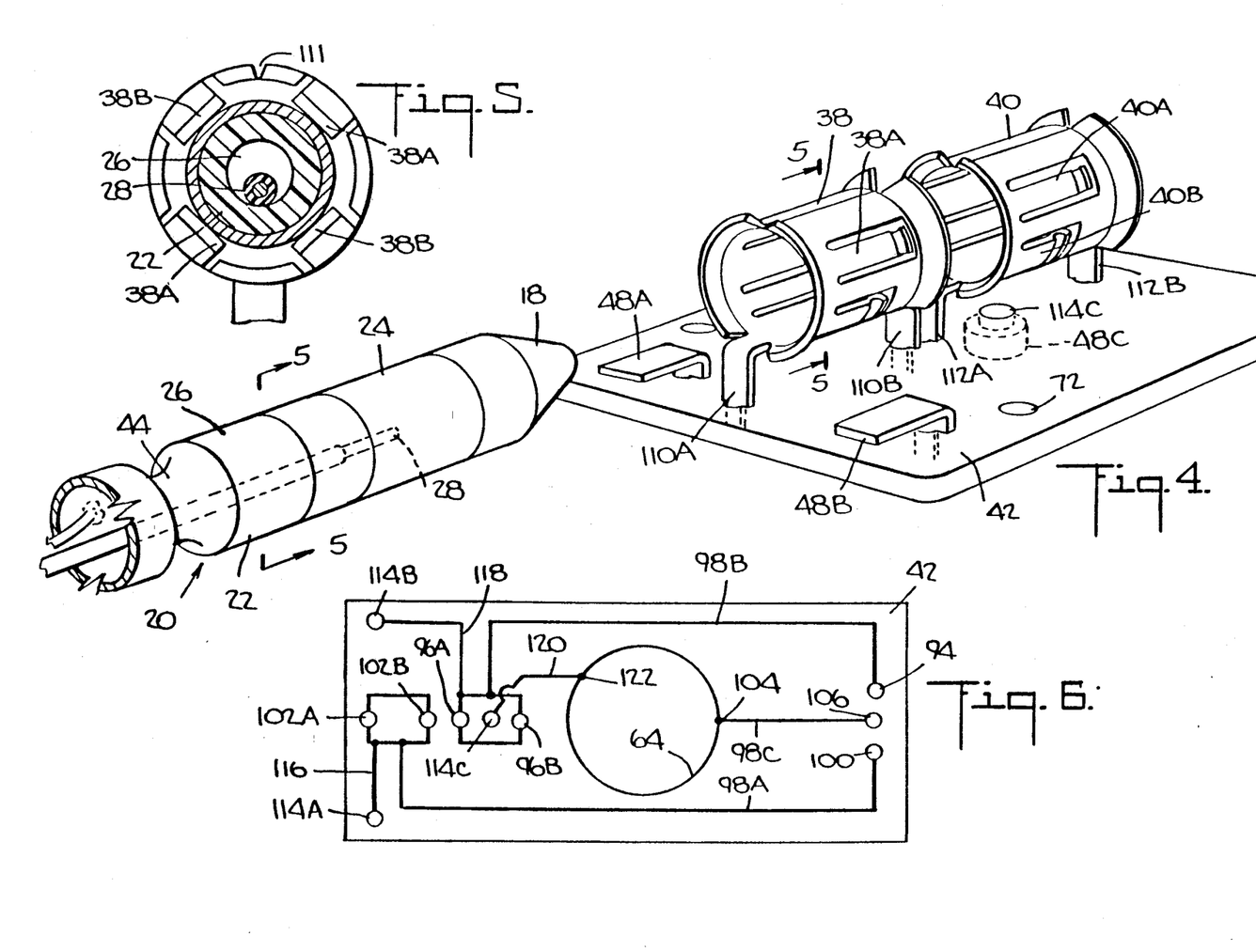
FIG. 4 shows a perspective view of the connector of FIG. 1 and the printed circuit board of FIG. 3.
FIG. 5 shows a cross-sectional view across section lines 5—5 of FIG. 4 after insertion of the connector into the opening in the housing of the leg plate.
FIG. 6 shows a schematic view of the printed circuit board of FIG. 3 in accordance with the invention.

Referring to FIGS. 1 and 5, the connector 20 has a forward tapered tip 18 and two electrically conductive terminals 22, 24. The terminals 22, 24 are spaced from each other and attached to the respective proximal ends 26, 28 of the twisted wire pair 8. A leg plate 30 has a housing 32 with an opening 34 in which is inserted the connector 20.

Within the opening 34 are two fingers 38A of a front barrel contact 38 and two fingers 40A in a rear barrel contact 40. The two fingers 38A are diametrically opposite each other, as are the two fingers 40A. The barrel contacts are each cylindrical and mounted on a printed circuit board (PCB) 42 and have open ends in line with each other. Barrel contact 38 is between the entrance of the opening 34 and the other barrel contact 40. The front and rear barrel contacts are identical and constitute input contacts.

Each of the two fingers 38A, 40A have respective free ends which are convexly curved. Upon full insertion of the connector 20 through the open ends of both barrel contacts 38 and 40, the free ends of the fingers 38A, 40A respectively engage the terminals 22, 24 and exert about a quarter pound force on the connector because the diameter of the connector is wider than the inner diametrical width defined between the diametrically spaced apart fingers 38A, 40A when the fingers are in an untensioned state.

The barrel contact 40 also has a pair of two diametrically opposite fingers 40B each with a convexly curved free end that biases into contact with the terminal 24 of connector 20 upon full insertion of the connector 20 into the barrel contacts 38, 40. The barrel contact 38 also has a pair of two diametrically opposite fingers 38B each with a convexly curved free end that biases into contact with a recess 44; that is, this free end clicks into place in the recess. The recess 44 is curved and extends about the outer circumference of the connector 20.

This clicking into place of fingers 38B with recess 44 causes a sudden change in resistance to further advancing movement of the connector in the leg plate and is noticeably felt by the person who is inserting the connector. This signifies to such person that full insertion has been attained and that electrical connection between the terminals 22, 24 and the barrel contacts 38, 40 has been established.

As further confirmation that the connector 20 has been fully inserted, an interior wall 46 of the housing 32 (see FIG. 2) is arranged directly at the end of the path of insertion of the connector 20. When the tapered tip 18 of the connector 20 (see FIGS. 2 and 4) contacts this wall 46, it is effectively blocked by the wall 46, thereby also signifying full insertion of the connector 20 into the barrel contacts 38, 40 and preventing any further advance of the connector 20 into the leg plate.

As described, it may be appreciated that the connector 20 constitutes a plug and the opening 34 with barrel contacts 38, 40 constitutes a socket. Thus, the plug is inserted into the socket for establishing electrical connection therebetween.

Figure 3:
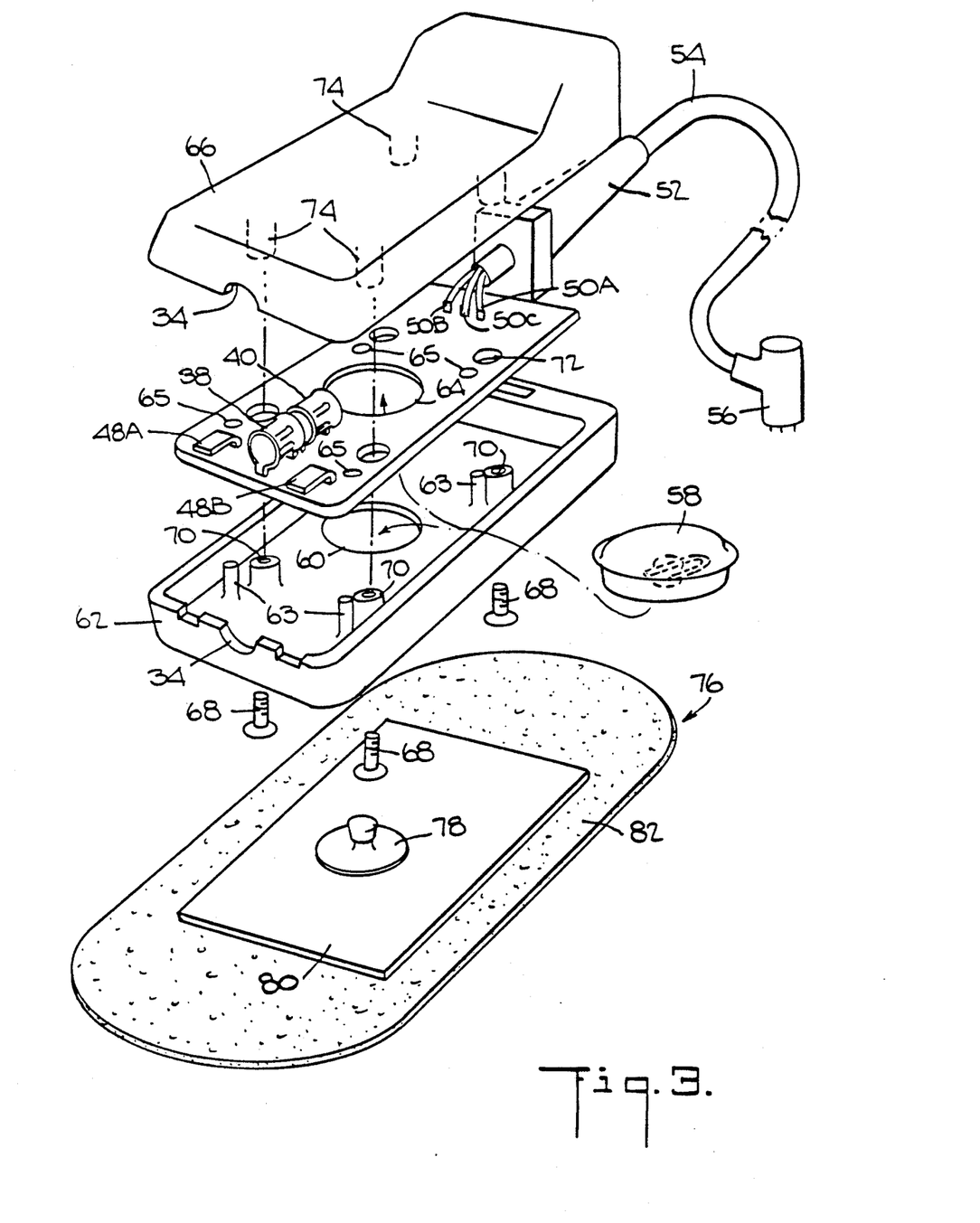
FIG. 3 shows an exploded perspective view of the leg plate assembly of the connector device of FIG. 1.

FIG. 3 is illustrative of the method of assembly of the leg plate. The barrel contacts 38, 40, the test terminals 48A, 48B and 48C (see FIG. 4), and the three output leads 50A, B, C are all soldered onto PCB 42. The output leads 50A, B, C extend from PCB 42 through shielded cable 54, which leads to a plug 56. After assembly is completed, the output leads 50a, 50b, and 50c extend from PCB 42 through strain relief 52 via a shielded cable 54 and plug 56 to the fetal monitor.

Next, a snap compartment 58 is secured within an opening 60 in the bottom half 62 of the housing or in the opening 64 in the PCB 42. If the snap compartment 58 is secured to the PCB 42, care must be taken to avoid fracture of the PCB 42 from stresses acting on the PCB during snapping engagement.

The housing bottom and top halves 62, 66 are brought together to enclose the PCB 42. The PCB 42 is secured to the bottom housing 62 by ultrasonic staking the four plastic studs 63 after they go through respective mating holes 65 in PCB 42. Staking involves melting the ends of the plastic studs ultrasonically onto the PCB 42, which ensures that alignment of opening 34 with contacts 38, 40 is permanent. The stems of four screws 68 are inserted through respective hollow bosses 70 in the bottom half 62 and through respective holes 72 in the PCB 42 that are aligned with the hollow bosses 70. The stems of the screws 68 are then screwed into threaded bosses 74 which extend from the underside of the upper half 66. In this manner, the housing halves 62, 66 become secured with each other. Test terminals 48A, 48B and 48C protrude out of the housing.

The assembled housing 32, which has a rectangular bed-like shape as seen in FIG. 1, is then ready to be secured to the base 76 by engaging a snap stud 78 into the opening in the snap compartment 58. The snap stud 78 may be considered a ground electrode and has two plate portions 78A, 78B (see FIG. 2). Between the plate portions 78A, 78B is held a center portion of a vinyl board 80. An adhesively coated flexible foam pad 82 is secured to the underside of the vinyl board 80 and has a central circular opening beneath the plate portion 78A. A conductive gel 84 is arranged in this central circular opening and is mixed with a reticulated foam.

The vinyl board 80 is rectangular as is the bottom surface of the bottom half 62 of the housing 32. When the sides of each are aligned with each other, the snap stud 78 is aligned with the receiving hole of the snap compartment 58. Effecting snapping engagement between the housing 32 and the base 76 when the base 76 is secured to the patient's leg may be done readily by aligning the sides of the lower housing half 62 with the sides of the vinyl board, which in turn aligns snap compartment 58 with the snap stud 78. The size of the surfaces of the vinyl board and bottom housing half 62 which face each other need not be the same size; the size of the surface of the vinyl board may be slightly larger and still be able to be a guide for alignment to effect snapping engagement. Further, these surfaces need not be rectangular, but it is preferred that they conform in shape with each other.

Figure 7:
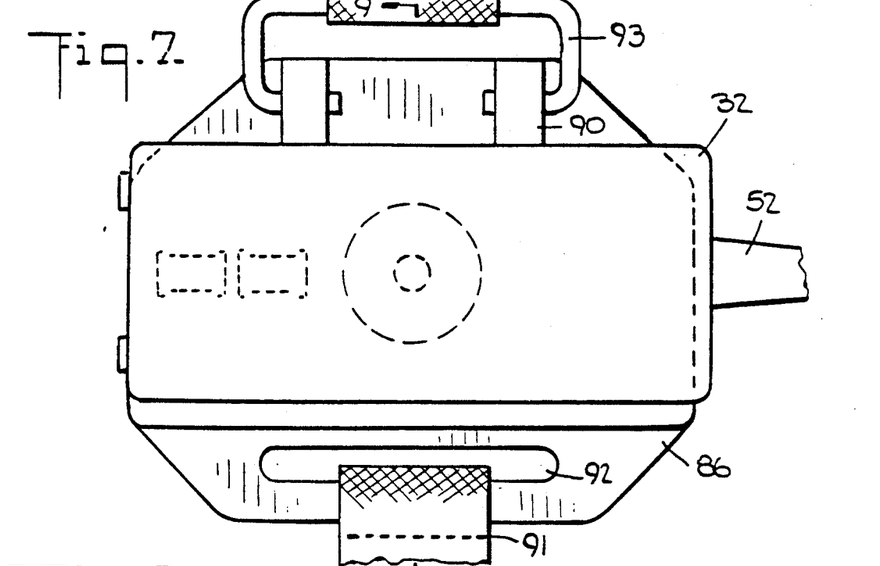
FIG. 7 shows a top view of a second embodiment of the connector device in accordance with the invention.
Figure 8:
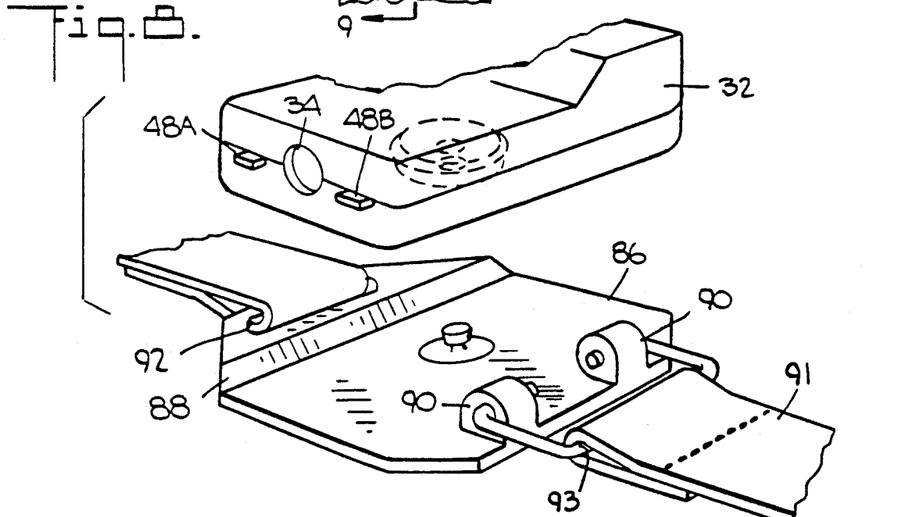
FIG. 8 shows a perspective view of the base of FIG. 7 with the leg plate housing of FIG. 1 over the base. A clip for the belt is a variation of the clip of FIG. 7.
Figure 9:
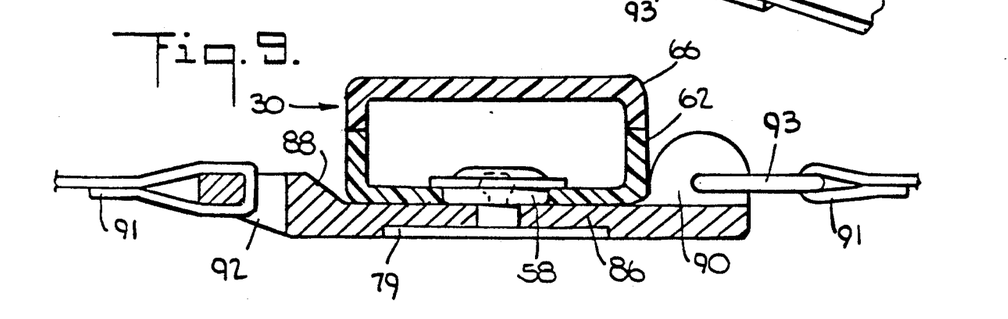
FIG. 9 shows a cross-sectional view across section lines 9—9 of FIG. 7 after assembly of the housing onto the base.

FIGS. 7, 8 and 9 show an alternative embodiment in which the same assembled housing 32 is secured to a different base 86, which has its own snap stud 78 for effecting snapping engagement in a like manner as that for base 76 of FIG. 3. Projection 88 extends upward from the base 86 adjacent to a side of the housing 32 so as to block relative rotation of the housing 32 on the snap 78 by blocking the corners of the housing.

Belt clasp holders 90 are provided on one side of the base 86 and a slot 92 is provided on the opposite side of the base 86. A belt 91 has an end which is looped through the slot 92 and is wrapped around a patient's leg. FIG. 8 shows a clasp 93 having free ends inserted through respective aligned holes in the belt clasp holders 90 and has a central segment inserted through a loop at another end of the belt. The free ends may point inwardly as shown or else outwardly. In both cases, the clasp may be resiliently bendable plastic or else made of rigid metal and be permanent.

The belt holders 90 also block relative rotation of the housing 32 on the base 86 because they project upward from the base 86 adjacent to another side of the housing 32. Together, projection 88 and belt holders 90 serve as guides for placement of the housing 32 on the base 86 by defining an area therebetween on the base 86 for receiving the housing. Preferably, this area conforms in shape to the underside of the housing bottom half 62.

FIG. 6 shows that the printed circuit board 42 has three conductive tracers 98A, 98B, 98C. The first conductive tracer 98A extends between output terminal 100 and input terminals 102A, 102B. The second conductive tracer 98B extends between output terminal 94 and input terminals 96A, 96B. The third conductive tracer 98C extends between ground ring terminal 104 and output terminal 106.

Referring to FIGS. 3, 4 and 6, it can appreciated that the three output leads 50A, B, C are respectively soldered to output terminals 100, 94 and 106. Two bent legs 110A, 110B of barrel contact 38 are respectively soldered to input terminals 102A, 102B. Two bent legs 112A, 112B of barrel contact 40 are respectively soldered to input terminals 96A, 96B.

The legs of the barrel contacts 38, 40 are subject to fatigue from vibrations caused by repetitive insertion and removal of the connector 20 in the barrel contacts 38, 40. By having both legs in electrical contact with a tracer, electrical connection is maintained as long as at least one leg remains unbroken and in electrical connection. Each barrel contact should be able to withstand 5000 cycles of insertion and removal of the connector 20 without breakage.

The barrel contacts 38, 40 are identical to each other for sake of economy in manufacture. Fabrication of the barrel contacts 38, 40 involves feeding a sheet of metal, such as beryllium copper, through a progressive stamping die, which stamps the sheet metal into its final shape. The stamped sheet is then heat treated by heating for strengthening.

For barrel contact 38, for instance, cut outs are made in the metal sheet by the progressive stamping die to define the fingers 38A, B and the legs 110A, B. Next, the free ends of the fingers are convexly curved to project from one face of the sheet and the legs are bent to project from the opposite face. The sheet is then bent into a cylindrical shape as shown in FIG. 4 to form a hollow barrel contact whose ends are brought together to form a V-like space 111 as shown at the top of FIG. 5. The fingers project inwardly and the legs project outwardly. The barrel contacts are gold plated for providing corrosion and wear resistance. The fingers 38A,B and 40A,B are resilient so that their convexly curved free ends bias inwardly when forced outwardly upon insertion of the connector 20 into the barrel contacts 38, 40.

Of course, it is not actually necessary for barrel contact 40 to have two sets of pairs of fingers 40A, 40B; either pairs of fingers 40A or pairs of fingers 40B will suffice for establishing contact with terminal 24. However, if the barrel contacts are identical, the same progressive stamping die may be used.

After insertion of the connector 20 into the opening 34, electrical contact is established between the terminals 22, 24 and the barrel contacts 38, 40, respectively. In this manner, an electrical circuit path is made between the fetal electrode 10, one respective twisted wire 8, terminal 22, barrel contact 38, tracer 98A and output terminal 100. An electrical circuit path is also made between the maternal electrode 12, the other twisted wire 8, terminal 24, barrel contact 40, tracer 98B and output terminal 94. Another electrical circuit path is made between the snap stud 78, the snap compartment 58, the ground ring terminal 104, the tracer 98C and the output terminal 106. The ground ring terminal 104 extends about the circumference of the opening 64 to form a ring and is covered by solder.

Preferably, the output leads 50A, B, C are color coded; e.g., the lead 50B from output terminal 94 may be blue, the lead 50A from output terminal 100 may be red and the lead 50C from output terminal 106 may be white. In this manner, the blue lead 50B is associated with the maternal electrode 12; the red lead 50A is associated with the fetal electrode 10; and the white lead 50C is associated with the ground electrode, e.g., plate portion 78A. This helps to ensure recognition of the leads from each other during assembly of plug 56.

It should be appreciated that the construction of the connector and leg plate as described helps to avoid the possibility of inadvertently mixing up interconnecting wires, and does so without relying on color coding (other than for the output leads). Since the tracer terminals lie directly beneath the components to which that are to be electrically connected, the potential for confusion in making the correct electrical connection therebetween is obviated.

Further, correspondence between the output leads and the spiral and maternal electrodes is assured by maintaining the relative position of the terminals themselves. Since the fetal electrode 10 is arranged further forward at the forward wire end 2 than is the maternal electrode 12, the connector terminal 22 is arranged further forward towards the forward wire end 2 and closer to the fetal electrode 10 than is connector terminal 24. The correspondence between the fetal and maternal electrodes and their respective connector terminals thereby becomes evident by inspection without the need for color coding the twisted wire pair.

In addition, the relative arrangement of the barrel contacts 38, 40 with respect to each other is arranged in a like manner, i.e., barrel contact 38 is further forward (closer to the entrance of the opening 34) than is barrel contact 40. Thus, when the connector is inserted into barrel contacts 38, 40, the first barrel contact which the connector passes through is barrel contact 38. After full insertion of the connector 20 in the opening 34, the connector terminal 22 makes electrical connection with barrel contact 38, thereby associating barrel contact 38 with fetal electrode 10. Similarly, barrel contact 40 becomes associated with maternal electrode 12.

Conductive tracers 98A, 98b extend from their respective connection with the barrel contacts 38, 40 to terminate at the respective output terminals 100, 94, which are spaced from either side of output terminal 106. Thus, the association between the output terminals and the respective electrode can be readily made by referring to FIGS. 4 and 6 which illustrate the connections between the output terminal and the barrel contact.

FIGS. 10-13 show a connector device for testing purposes in which test terminals 48A, 48B and 48C are electrically connected, respectively, with the barrel contacts 38, 40 and snap compartment 58. Test terminals 48A, 48B, 48C are soldered to respective test contacts 114A, 114B, 114C. The test tracer 116 extends between input terminals 102A, 102B and the test contact 114A. The test tracer 118 extends between input terminals 96A, 96B and the test contact 114B. The test tracer 120 extends between test input terminal 122 and the test contact 114C. Test input terminal 122 is part of ground ring terminal 104 and thereby electrically connects test contact 114C and tracer 120 with the snap compartment 58 and the opening 64, which serves here as a compartment seat.

Figures 10, 11:
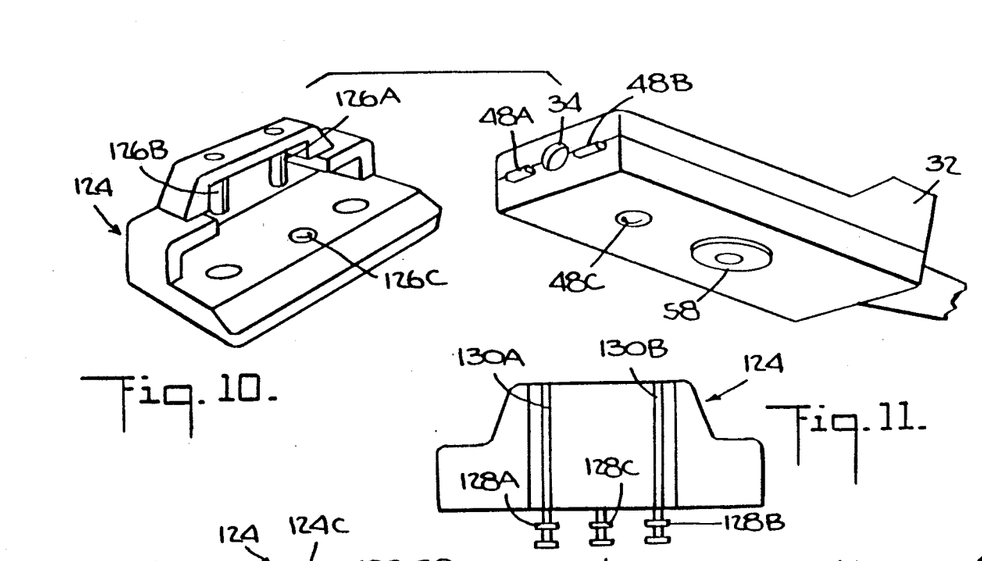
FIG. 10 shows a perspective view of the leg plate housing of FIG. 1 and a test adapter in accordance with the invention.
FIG. 11 shows a rear elevation view of the test adapter depicted in FIG. 10.
Figure 12:
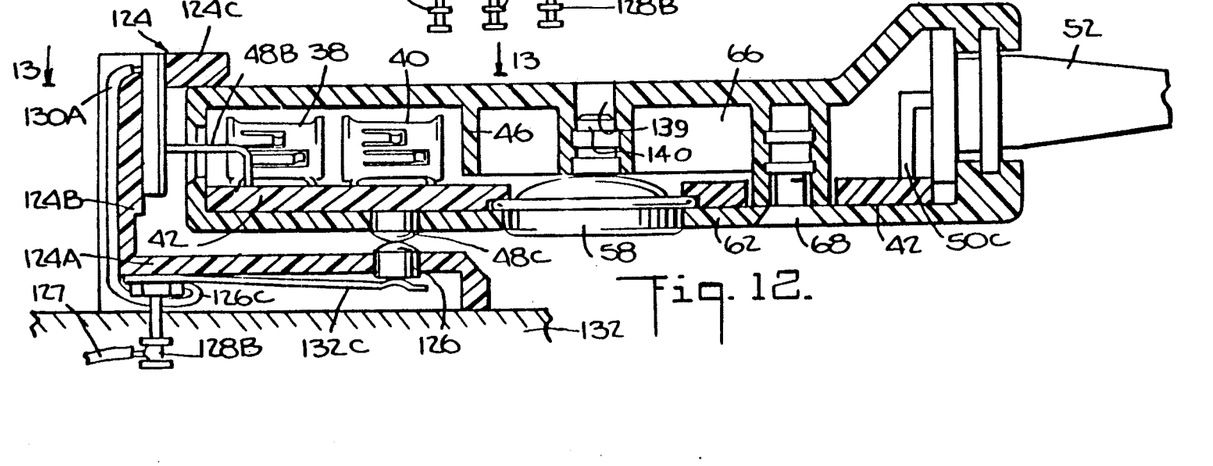
FIG. 12 shows a cross-sectional view across section lines 12—12 of FIG. 13 with the leg plate housing shown inserted into a test adapter.
Figure 13:
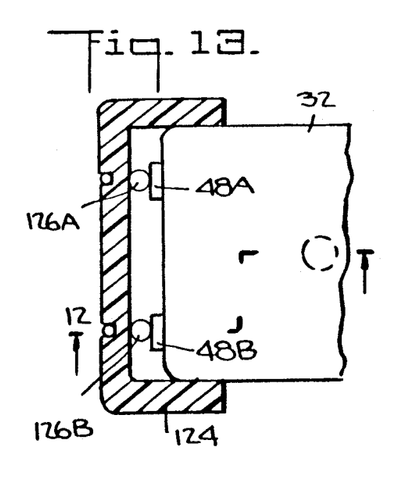
FIG. 13 shows a partial cross-sectional view across section lines 13—13 of FIG. 12.

Test terminals 48A and 48B project from one end of the housing 32 and test terminal 48C projects from the underside of the housing 32. The end of the housing with the test terminals 48A, B is inserted, for test purposes, into an adapter 124 attached to the rear of a fetal monitor. As shown, the opening 34 is free of the connector 20.

The adapter 124 has a long side 124A, an end side 124B, and a short side 124C. The long and short sides 124A, C are substantially parallel to each other and the end side 124B extends therebetween. The end side of the housing with the test terminals 48A, 48B is against the end side 124B of the adapter 124 for enabling the test terminals 48A, B to make electrical connection with adapter contacts 126A, 126B, respectively. The housing is retained in place in the adapter by gravity. The top housing 66 is guided against an inner facing surface of the short side 124A while the test terminal 48C presses into contact with the adapter contact 126C protruding inwardly from the long side 124A.

The adapter contacts 126A, B, C are in respective electrical connection with contact pins 128A, B, C at the underside of the adapter 124 via respective conductive elements 130A, B, C. The rear side of the fetal monitor has three mating terminals 127 (only one shown) which mate respectively with the three contact pins 128A, 128B, 128C as the housing is inserted into the adapter 124.

A simulated R-wave signal is transmitted from the fetal monitor via the mating terminals 127. This simulated R-wave signal is typical of an EKG or ECG signal and has approximately 100 millivolt peak-to-peak amplitude at a rate of 120 beats per minute.

In so doing, three test paths may be checked. The three test paths include the respective test terminals 48A, B, C; tracers 116, 118, 120; tracers 98A, 98B, 98C; output terminals 100, 94, 106; output leads 50A, B, C; cable 54; plug 56; fetal monitor electronics (not shown), a monitor display (not shown), and a monitor chart recorder (not shown).

If any of the three test paths are open, the monitor will not count the beat of the simulated R-wave that should be received by the fetal monitor after its transmission. This is because either there is no signal being developed at an amplifier input of the fetal monitor or there is a return path open downstream of the amplifier input which causes the amplifier input to saturate.

An operator of the fetal monitor recognizes the count signal if the leg plate passes the test. The leg plate connector and fetal monitor may then be used since the possibility of equipment malfunction is ruled out. Otherwise, if the count can not be recognized, servicing is required.

If the leg plate connector passes the test and the connector device still does not function properly, then the cause for the problem at least has been somewhat isolated, i.e., the problem is either that the grounding is poor, stray capacitance is affecting the twisted wire pair too much, or the barrel contacts are too dirty or their legs have broken. The grounding may be improved by adding more conductive gel 84. The stray capacitance problem may be remedied by replacing the twisted wire pair and connector. If the legs of the barrel contacts have broken, then servicing is required The contacts 38, and 40 and snap compartment 58 may be used of the associated test leads 48A, B, C for test purposes by modifying the adaptor so that any of its adapter contacts 126A, B or C are repositioned and project further outwardly to effect electrical connection with any of the contacts 38 or 40 or snap compartment, respectively.

The adapter 124 may be further modified to accommodate insertion of the housing with its base attached. In this case, either a ground test terminal extends through the base in contact with the test lead 48C or the ground electrode in the base itself is used for electrically connecting with the adapter contact 126C. The ground electrode itself may be used in this manner preferably only if the conductive gel 84 is to be added later.

Figure 2:
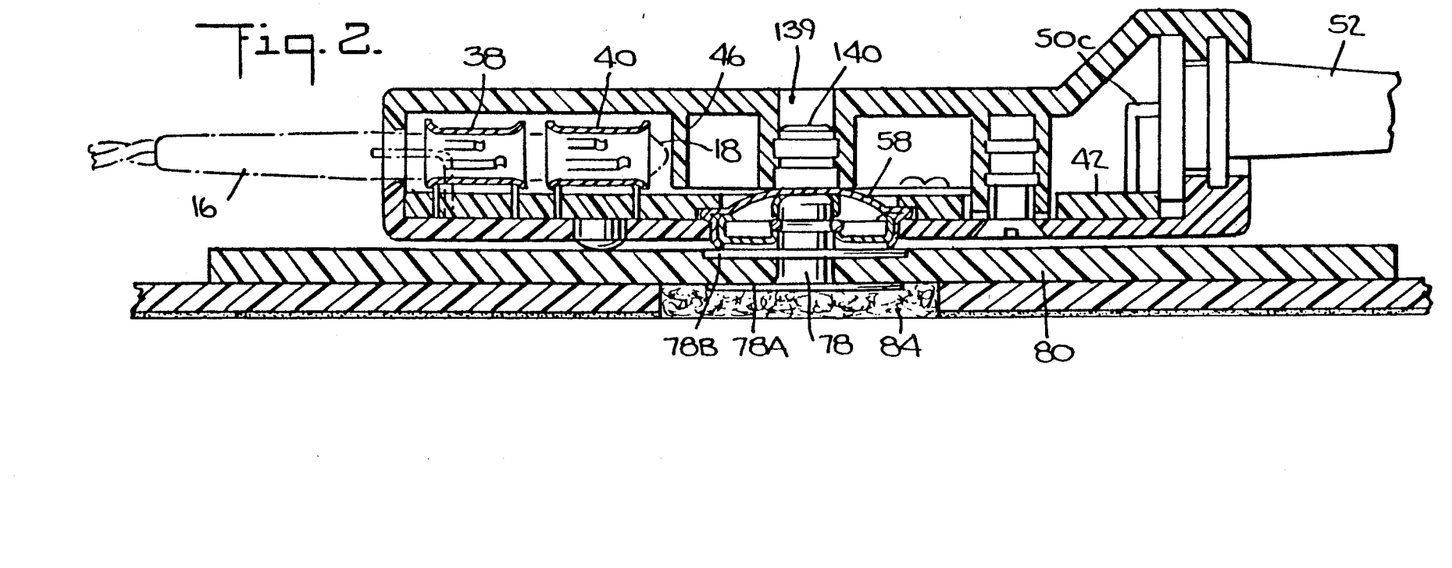
FIG. 2 shows a cross-sectional view across section lines 2—2 of FIG. 1.
Figure 14:
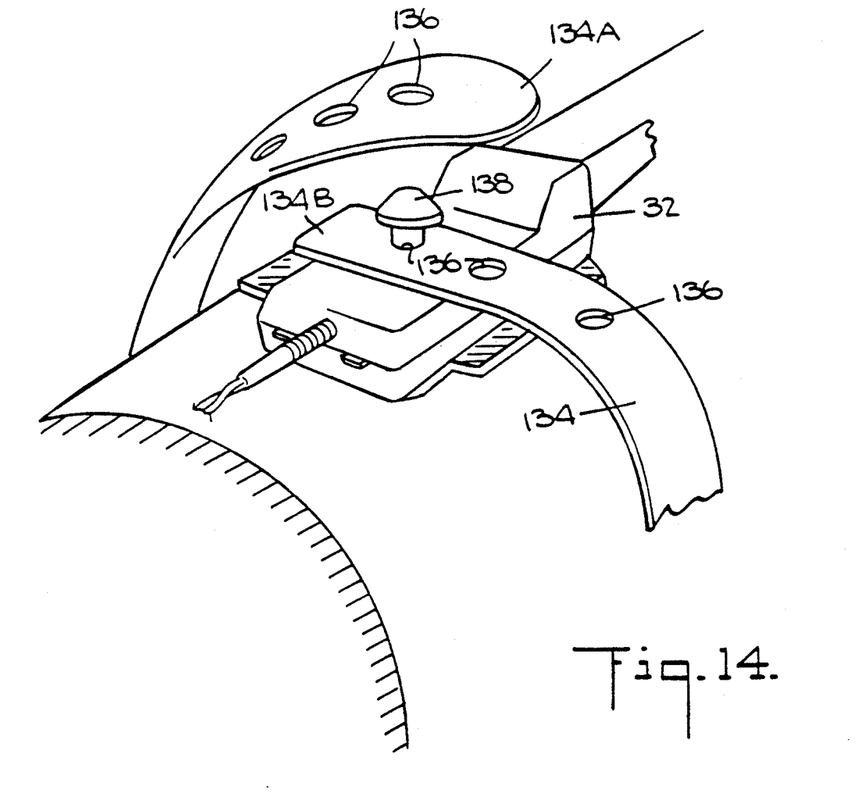
FIG. 14 shows a perspective view of a third embodiment of the invention in which the attachment of the belt to the housing varies from the other embodiments and is shown arranged on a leg of a patient.
Figure 15:
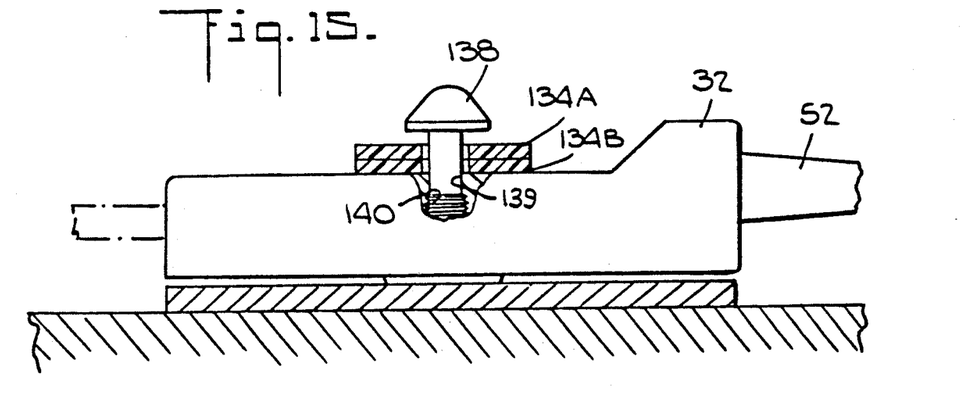
FIG. 15 shows a partially broken side elevation view of the embodiment of FIG. 14.

FIGS. 14 and 15 show another embodiment similar to that of FIG. 8, except that a buttonhole belt 134 with button holes 136 is wrapped around a patient's leg. One hole at each end 134A, 134B of the belt 134 is fitted onto a mushroom hat 138. The hat protrudes from the housing 32 from a hole 139 and is threadably engaged with a threaded socket 140 in the housing 32. The diameter of the holes is slightly larger or about the same size as the widest diameter of the hat 138. The bottom of socket 140 is insulated to prevent electrical connection with the snap compartment 58. FIGS. 1 and 2 also show the hole 139 and the socket 140.

Figure 16:
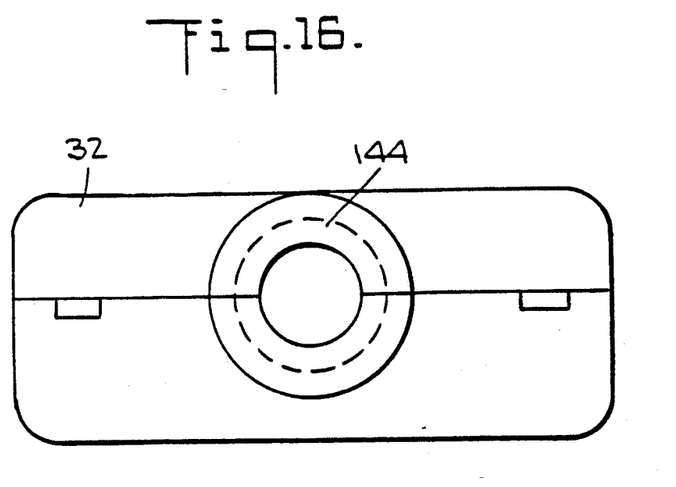
FIG. 16 is a front end view of the leg plate in accordance with another embodiment which is an "O" ring seal that works with the connector plug of the spiral.
Figure 17:
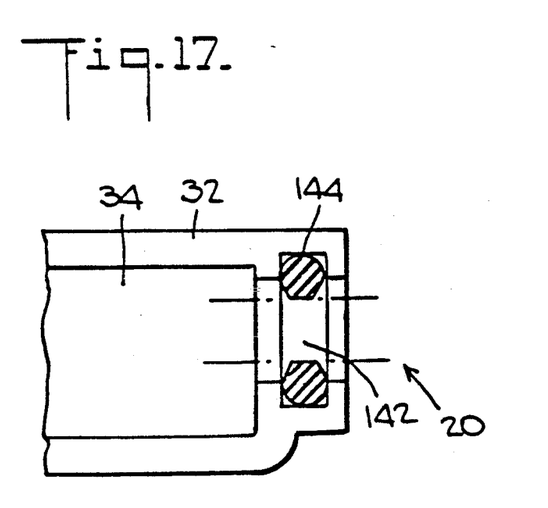
FIG. 17 is a partial longitudinal cross-sectional view of FIG. 16.

FIGS. 16–17 show an optional arrangement which may be used for any of the other embodiments. The entrance of the opening 34 of the housing 32 is modified to provide a chamber 142 in which is arranged an O-ring seal 144, which made of an elastic material. The tapered tip 18 of the connector 20 is inserted through the inner space defined by the O-ring seal 144 in order to reach the barrel contacts 38, 40. As the tapered tip 18 is inserted, the O-ring seal 144 is compressed outward and follows the diameter of the connector 20, thereby wiping the outer surface of the connector 20 clean of contaminants. At the recess 44, the O-ring seal 144 is free to expand again to its relaxed state but is again compressed outward as the connector 20 is inserted further into the opening 34. By virtue of the O-ring seal 144 rubbing the outer surface of the connector 20, contaminants that are on the connector 20 are prevented from contaminating the barrel contacts 38, 40 in the opening 34.

It should be understood that the engagement between the recess of the connector and the finger of the barrel contact may be made instead by providing the connector with the finger and the barrel contact with the recess. In addition, analogous components of any embodiment are interchangeable with those from the other embodiments or those found in U.S. patent application Ser. No. 605,843.

Figure 18:
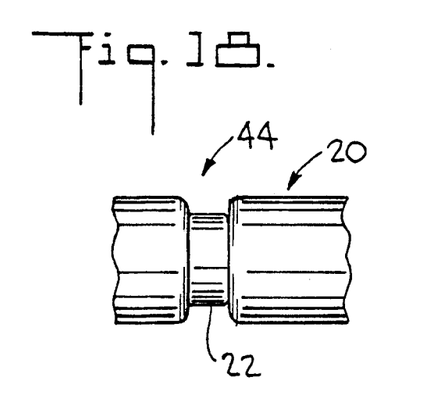
FIG. 18 is a diagrammatic partial side view of another embodiment of the connector.

Further, the finger 38A on barrel contact 38 alone could serve not only for engaging with the recess 44, but also serve to effect electrical connection with terminal 22 where terminal 22 is arranged within the recess 44 as shown in FIG. 18.

It is preferred, however, that an identical recess to that of recess 44 be added to the connector 20 between terminals 22 and 24 to enable the fingers 38A, 40A to click into place in both recesses simultaneously. This is preferred for keeping the unit held together during the fabrication process. Thus, when used, a user would have to listen for two clicks before knowing that full insertion had been made. That is, the first click arises from finger 38A entering into the newly added recess and the second click arises from the simultaneous click of finger 38A entering into recess 44 and finger 40A entering into the newly added recess.

While the foregoing description and drawings represent the preferred embodiments of the present invention, it will be understood that various changes and modifications may be made without departing from the spirit and scope of the present invention.

What is claimed is:

1. A connector device for use in monitoring fetal heart rate, comprising:
a housing;
two input contacts spaced from each other and supported by the housing;
a printed circuit board within said housing and having at least two input terminals spaced from each other, a ground terminal spaced from said input terminals, three output terminals spaced from each other, and three conductive tracers arranged for electrically connecting said three output terminals respectively, with said two input terminals and said ground terminal, said two input contacts each being in electrical connection with a respective one of said two input terminals; and
means for securing said housing to a base, said securing means being in electrical connection with said ground terminal, said securing means including a conductive element retained against said printed circuit board and being in electrical connection with said ground terminal.

2. A device as in claim 1, further comprising:
a bas which has a ground electrode, said securing means securing said housing to said base, said base having means for releasably securing said housing in position on a patient, and means for releasably and electrically connecting said ground electrode to said securing means.

3. A device as in claim 2, wherein said base has retaining means adapted for retaining ends of a belt; further comprising a belt with ends retained by said retaining means.

4. A device as in claim 2, wherein said securing means includes means for enabling said housing to rotate relative to said base.

5. A device as in claim 1, wherein said housing has a projection adapted for engaging belt holes; further comprising a belt with a belt hole engaging said projection.

6. A device as in claim 1, further comprising:
a plug connector, said housing having an opening constituting a socket for accommodating insertion of said plug connector therein, said plug connector having two connector terminals spaced from each other and which are in electrical connection respectively with two wires of a twisted wire pair, said two connector terminals establishing electrical connection respectively with said two input contacts, respectively, upon insertion of said plug connector as far as possible within said opening; and
means for releasably securing said plug connector in position in said opening when said plug connector reaches a location where said two connector terminals have established said electrical connection with said input contacts, respectively.

7. A device as in claim 1, wherein said printed circuit board has an opening through which extends the conductive element.

8. A device as in claim 1, wherein said conductive element has means for making snapping engagement with a conductive element from the base.

9. A connector device for use in monitoring fetal heart rate, comprising:
a housing having sides with corners;
two input contacts spaced from each other and supported by the housing;
a printed circuit board within said housing and having at least two input terminals spaced from each other, a ground terminal spaced from said input terminals, three output terminals spaced from each other, and three conductive tracers arranged for electrically connecting said three output terminals, respectively, with said two input terminals and said ground terminal, said two input contacts each being in electrical connection with a respective one of said two input terminals;

means for securing said housing to a base, said securing means being in electrical connection with said ground terminals;

a base which has a ground electrode, said securing means securing said housing to said base, said base having means for releasably and electrically connecting said ground electrode to said securing means, said securing means including means for enabling said housing to rotate relative to said base; and means for blocking said housing from rotating relative to said base, said blocking means including projections extending from said base to project adjacent to said sides of said housing when said housing is releasably secured to said base, said projections being arranged to block rotation of said housing relative to said base 10. A connector device for use in monitoring fetal heart rate, comprising:

a housing;

two input contacts spaced from each other and supported by the housing;

a printed circuit board within said housing and having at least two input terminals spaced from each other, a ground terminal spaced from said input terminals, three output terminals spaced from each other, and three conductive tracers arranged for electrically connecting said three output terminals respectively, with said two input terminals and said ground terminal, said two input contacts each being in electrical connection with a respective one of said two input terminals;

means for securing said housing to a base, said securing means being in electrical connection with said ground terminal; and two conductive test terminals which are accessible from outside said housing, said test terminals being in electrical contact with two of said conductive tracers, respectively, that are in electrical connection with said two input terminals.

11. A device as in claim 10, wherein said securing means include a snap compartment which has a snap opening adapted for holding a snap stud therein, said snap stud having a base portion, further comprising:

another conductive test terminal on said board that is accessible from outside said housing for establishing electrical connection therewith, said another conductive terminal being in electrical contact with said snap compartment; and an adapter with three terminals in electrical contact, respectively, with said two conductive test terminals and said another conductive test terminal.

12. A connector device for use in monitoring fetal heart rate, comprising:

a housing;

two input contacts spaced from each other and supported by the housing, said two input contacts being first and second barrel contacts spaced from each other and having a pair of fingers diametrically opposite each other;

a printed circuit board within said housing and having at least two input terminals spaced from each other, a ground terminal spaced from said input terminals, three output terminals spaced from each other, and three conductive tracers arranged for electrically connecting said three output terminals respectively, with said two input terminals and said ground terminal, said two input contacts each being in electrical connection with a respective one of said two input terminals;

means for securing said housing to a base, said securing means being in electrical connection with said ground terminal;

a plug connector, said housing having an opening constituting a socket for accommodating insertion of said plug connector therein, said plug connector having two connector terminals spaced from each other and which are in electrical connection respectively with two wires of a twisted wire pair, said two connector terminals each establishing electrical connection with a respective one of said two input contacts upon insertion of said plug connector as far as possible within said opening, a first pair of said fingers of said first barrel contact having a free end engaging a recess on an outer circumference of said plug connector, a second pair of said fingers of said first barrel contact being in electrical contact with a first of said two connector terminals, said second barrel contact having a pair of fingers in electrical contact with a second of said two connector terminals; and means for releasably securing said plug connector in position in said opening when said plug connector reaches a location where said two connector terminals have established said electrical connection with said input contacts, respectively.

13. A connector device for use in monitoring fetal heart rate, comprising:

a housing having an elongated opening with an entrance;

two input contacts spaced from each other and supported by the housing;

a printed circuit board within said housing and having at least two input terminals spaced from each other, a ground terminal spaced from said input terminals, three output terminals spaced from each other, and three conductive tracers arranged for electrically connecting said three output terminals respectively, with said two input terminals and said ground terminal, said two input contacts each being in electrical connection with a respective one of said two input terminals, one of said two input contacts being located between said entrance and the other of said two input contacts; and means for securing said housing to a base, said securing means being in electrical connection with said ground terminal.

14. A connector device for use in monitoring fetal heart rate, comprising:

a housing;

two input contacts spaced from each other and supported by the housing;

a printed circuit board within said housing and having at least two input terminals spaced from each other, a ground terminal spaced from said input terminals, three output terminals spaced from each other, and three conductive tracers arranged for electrically connecting said three output terminals respectively, with said two input terminals and said ground terminal, said two input contacts each being in electrical connection with a respective one of said two input terminals;

means for securing said housing to a base, said securing means being in electrical connection with said ground terminal; and a base which has a ground electrode, said securing means securing said housing to said base, said base having means for releasably and electrically connecting said ground electrode to said securing means, said securing means including means for enabling said housing to rotate relative to said base, said base and said housing each having a respective surface that faces and conforms in shape with each other.

15. A connector device for use in monitoring fetal heart rate, comprising:

fetal and maternal electrodes;

a plug connector with two terminals spaced from each other, said plug connector being sized to allow removal of the plug connector from within a driving tube having a dimension suitable for use in placing the fetal and maternal electrodes into position within an expectant mother;

two wires each connecting a respective of the two terminals with a respective one of the fetal and maternal electrodes;

a support assembly having a housing, the housing having an elongated socket opening;

a socket connector having first and second input terminals;

a ground terminal, each of said input and ground terminals being supported by the housing and electrically isolated from each other;

first, second and third output terminals each supported by the housing and electrically isolated from each other;

three conductive paths within the housing, a first of the conductive paths extending from the first input terminal to the first output terminal, a second of the conductive paths extending from the second input terminal to the second output terminal, a third of the conductive paths extending from the ground terminal to third output terminal; and locking means for locking the plug connector in a releasable manner within the socket opening and for simultaneously electrically connecting each of the two terminals of the plug connector with a respective one of the input terminals.

16. A device as in claim 15, further comprising a printed circuit board within said housing, said printed circuit board having three conductive tracers located within said three conductive paths, respectively.

17. A device as in claim 16, further comprising:

three test terminals in electrical connection, respectively, with said three conductive tracers; and an adapter retaining said housing and having three terminals in electrical connection, respectively, with said three test terminals.

18. A device as in claim 16, further comprising:

three test terminals in electrical connection, respectively, with said first and second conductive paths; and an adapter retaining said housing therein and having three contacts in electrical connection, respectively, with said two test terminals and said ground input.

19. A device as in claim 15, wherein said socket connector includes barrel contacts each with fingers which serve as the input terminals, said plug connector having an external periphery that has a recess, a free end of one of said fingers engaging with said recess for releasably retaining said plug connector in said barrel contacts.

20. A device as in claim 15, wherein said socket opening is accessible via an entrance in said housing, said housing defining a chamber adjacent to said entrance, said socket connector being within said opening, further comprising means arranged in said chamber for sealing said chamber from outside and for wiping said plug connector clean as the plug connector passes by said opening during insertion into the opening.

21. A connector device for use in monitoring fetal heart rate, comprising:

fetal and maternal electrodes spaced from each other;

a plug connector with two terminals spaced from each other;

a twisted wire pair respectively connecting said fetal and maternal electrodes with said two terminals;

a support assembly having a housing with a socket opening;

a contact supported by said housing and being within said socket opening, said contact having a finger with a free end;

means for releasably locking said plug connector within said socket opening said releasably locking means including a recess on an exterior periphery of said plug connector and into which may bias said free end of said finger; and an electrically conductive terminal within said recess.

22. A fetal electrode product for use in monitoring fetal heart rate, comprising:

a fetal electrode and a maternal electrode secured to a holder made of an insulating material;

an elongated flexible driving tube for rotating said holder;

a connector having an outer dimension less than an inner dimension of said driving tube so that said driving tube can be pulled over said connector after said fetal electrode has been attached to a fetus, said connector including at least two contacts separated and electrically isolated from each other, said connector having a proximate end and a distal end spaced from each other, one of the contacts being closer to the distal end than is the other of the contacts;

an elongated pair of insulated flexible wires each electrically connecting a respective one of the contacts with a respective one of the fetal and maternal electrodes, the wires extending through the proximate end of the connector; and means for relieving strain, the relieving strain means including a finned element through which extends the wires, said finned element extending from the proximate end of the connector.

* * * * *